US008523359B2

(12) United States Patent
Merz et al.

(10) Patent No.: US 8,523,359 B2
(45) Date of Patent: Sep. 3, 2013

(54) ILLUMINATION DEVICE AND OBSERVATION DEVICE

(75) Inventors: Franz Merz, Aalen (DE); Artur Hoegele, Oberkochen (DE); Peter Reimer, Ellwangen (DE)

(73) Assignee: Carl Zeiss Meditec AG, Jena (DE)

( * ) Notice: Subject to any disclaimer, the term of this patent is extended or adjusted under 35 U.S.C. 154(b) by 296 days.

(21) Appl. No.: 12/653,974

(22) Filed: Dec. 18, 2009

(65) Prior Publication Data

US 2010/0309433 A1 Dec. 9, 2010

Related U.S. Application Data

(60) Provisional application No. 61/203,090, filed on Dec. 18, 2008.

(51) Int. Cl.
*A61B 3/10* (2006.01)
*A61B 3/00* (2006.01)
*A61B 3/14* (2006.01)
*G02B 27/02* (2006.01)

(52) U.S. Cl.
USPC ........... 351/221; 351/200; 351/205; 351/210; 359/802

(58) Field of Classification Search
USPC ................. 351/221, 200, 205, 210, 222–223, 351/206, 208, 211, 214, 213; 359/802, 798, 359/803, 808, 816, 362, 375, 399, 404, 409, 359/431, 629, 640, 368, 381, 618, 636–639, 359/372, 389
See application file for complete search history.

(56) References Cited

U.S. PATENT DOCUMENTS 5,072,731 A * 12/1991 Taratuta et al. ............... 600/318
5,867,251 A 2/1999 Webb (Continued)

FOREIGN PATENT DOCUMENTS

DE 2 021 784 A 11/1970
DE 43 26 761 A1 2/1995

(Continued)

OTHER PUBLICATIONS

Harry Paul, Ed.: "Lexikon der Optik, Bd M bis Z" 2003, Springer Akademischer Verlag GmbH, Heidelberg, XP002439491.

*Primary Examiner* — Dawayne A Pinkney
(74) *Attorney, Agent, or Firm* — Kreigsman & Kreigsman

(57) ABSTRACT

An illumination device (10) is described for an observation device (100) having one, two or more observation beam paths (16, 17), each with at least one observation beam bundle, particularly for an operating microscope, the illumination device having at least one light source (11, 12) for producing at least one illumination beam path (14, 15) with at least one illumination beam bundle for illuminating an object to be observed, in particular, an eye to be observed, the illumination device (10) having at least one illumination optics unit, which has a collector (18, 22), and the at least one illumination beam path (14, 15) or the at least one illumination beam bundle running coaxially to an observation beam path (16, 17) or observation beam bundle. In order to create an illumination device that can be introduced with little structural complexity even in those cases where only a small structural space is available, it is provided according to the invention that light source (11, 12) lies in the front focal point of collector (18, 22) and is imaged on the fundus of the eye to be observed. In addition, a correspondingly improved observation device (100) is described.

20 Claims, 4 Drawing Sheets

(56) References Cited

U.S. PATENT DOCUMENTS

| | | | | |
|---|---|---|---|---|
| 6,003,993 | A | 12/1999 | Webb | |
| 2004/0057108 | A1* | 3/2004 | Namii | 359/385 |
| 2005/0128574 | A1* | 6/2005 | Reimer et al. | 359/389 |
| 2007/0268575 | A1* | 11/2007 | Yamazaki | 359/389 |
| 2009/0213329 | A1* | 8/2009 | Kandel et al. | 351/206 |

FOREIGN PATENT DOCUMENTS

| | | | |
|---|---|---|---|
| DE | 43 44 770 | A1 | 6/1995 |
| DE | 198 24 460 | A1 | 12/1999 |
| DE | 20 2004 019 849 | U1 | 3/2005 |
| DE | 10 2004 050 651 | A | 3/2006 |
| DE | 10 2006 013 761 | A1 | 9/2007 |
| WO | WO 02/26121 | A1 | 4/2002 |

* cited by examiner 100
10
13
14
16
11
21
24
17
15
19
18
20

26
30
100
19
14,15
16,17
20
11
21,24
27
13
10
18

100
30
13
10
23
15
12
16,17
20
22
29

10
18
100
19
11
16,17
14
25
13
28
20
16,17
12
15
23
22

ILLUMINATION DEVICE AND OBSERVATION DEVICE

CROSS-REFERENCE TO RELATED APPLICATIONS

The present application claims the benefit under 35 U.S.C. 119(e) of U.S. Provisional Patent Application No. 61/203,090, filed Dec. 18, 2008, the disclosure of which is incorporated herein by reference.

BACKGROUND OF THE INVENTION

The present invention relates first to an illumination device for an observation device according to the preamble of patent claim 1. In addition, the invention relates to an observation device according to the preamble of patent claim 17.

For example, an observation device may involve an operating microscope. In particular, the observation device can be designed as an ophthalmologic operating microscope, which is utilized, for example, for a special application in eye surgery, i.e., cataract surgery.

In the case of cataract surgery, a lens of the eye—which is clouded, for example, due to the cataract—is replaced by an artificial lens.

The lens of an eye is found inside a thin envelope, the so-called lens capsule. In order to remove the lens of the eye, access to the lens is created by a thin incision made in the lens capsule and the lens of the eye is next broken up into small pieces with a microsurgical instrument, and then these pieces are removed by means of an aspirating device.

This process takes place under microscopic observation—for example, under stereomicroscopic observation—employing a specially designed illumination device for such interventions. This illumination device presents both an illumination of the surrounding field, which is necessary for illuminating the entire operating field, as well as a red background illumination for the actual operating field limited to the pupil region of the lens of the eye, which is of decisive importance for the cataract operation. This red background illumination is based on the fraction of illuminating light, which, passing through the transparent media of the eye finally strikes the retina, which appears red due to good blood perfusion, is reflected therefrom, and then can also be observed, of course, as an apparent red background illumination, by the surgeon via the operating microscope. This very characteristic red background illumination in cataract surgery is generally known in professional circles under the term "red reflex".

For an optimal recognition of details relevant to the cataract operation, a red background illumination that is as homogeneous as possible has been proven to be a necessary prerequisite for the surgeon. A first requirement of the illumination device is thus to assure a homogeneity of the red reflex that is as optimal as possible over the entire pupil of the patient.

For complete elimination of the lens pieces of the lens of the eye, which has been broken up into tiny pieces, and for good recognition of transparent membranes, for example, of the lens capsule, another requirement must be fulfilled, that is, a good contrasting of phase objects and, in fact, this contrast should also be provided as much as possible over the entire pupil of the patient.

For surgery on the eye, and here, in particular, in cataract operations, a homogeneous, bright "red reflex" is required along with a good contrasting of phase objects over the entire region of the patient's pupil.

The operating microscopes of the prior art fulfill these requirements for regions of the pupil that are of varying size. A compromise must always be found between the primary requirements of a good, homogeneous "red reflex" and good contrasting of phase objects.

For the most part, illumination is provided at a small angle to the observation. This has the consequence, however, that the "red reflex" does not appear uniformly bright over the patient's pupil. An illuminating angle between 2 and 4 degrees has previously proven favorable. At this angle, one obtains a good compromise between good contrasting and illumination of the patient's pupil. Solutions, in which illumination is made at an angle to the observation, are described, for example, in DE 43 44 770 A1 or DE 20 2004 019 849 U1. With this arrangement, however, the "red reflex" reacts sensitively to a rolling of the patient's eye during the operation. Additional problems may occur when the patient's pupil is small or in connection with the refraction of the patient's eye. In the known solutions, therefore, the "red reflex" is not formed homogeneously.

For eye surgery, particularly in cataract surgeries, however, the surgeon requires a homogeneous, contrast-rich "red reflex".

Tests with coaxial illumination in fact led to a good, homogeneous "red reflex", but to a poor contrasting of phase objects, and thus previously have not proven suitable in practice. In this case, the illuminating optics unit was disposed in such a way that an illuminating mirror (or prism) lay between the two beam paths of the stereomicroscope. Thus, this did not involve an exact 0° illumination, which occurs precisely from the same direction as the observation.

One possibility for obtaining a homogeneous, bright "red reflex" with simultaneously good contrast can be achieved by providing an illumination device for an observation device having one, two or more observation beam paths, each with at least one observation beam bundle, in particular, for an operating microscope, having at least one light source for producing at least one illumination beam path with at least one illumination beam bundle for illuminating an object to be observed, in particular, an eye to be observed, whereby the illumination device has at least one illumination optics unit that is constructed according to the Köhler principle of illumination, and whereby the at least one illumination beam path or the at least one illumination beam bundle runs coaxially to an observation beam path or observation beam bundle. Such a solution is described, for example, in the older Application DE 10 2006 013 761.2 A1 of the Applicant.

In many cases, however, only a small structural space is present for the illumination device, so that an illumination optics unit, which is constructed according to the Köhler principle of illumination, cannot always be used.

SUMMARY OF THE INVENTION

Starting from the last-referred art, the object of the present invention is to further develop an illumination device and an observation device of the type named initially, in such a way that the illumination device can be introduced with little structural complexity even in those cases where only a small structural space is available.

This problem is solved according to the invention by the illumination device with the features according to the independent patent claim 1 and the observation device with the features according to the independent patent claim 17. Further features and details of the invention can be taken from the subclaims, the description and the drawings. Features and details, which are described in connection with the illumination device according to the invention, thus obviously also apply to the observation device according to the invention, and vice versa.

According to the first aspect of the invention, an illumination device is provided for an observation device having one, two or more observation beam paths, each with at least one observation beam bundle, particularly for an operating microscope, the illumination device having at least one light source for producing at least one illumination beam path with at least one illumination beam bundle for illuminating an object to be observed, in particular, an eye to be observed, the illumination device having at least one illumination optics unit, which has a collector, and the at least one illumination beam path or the at least one illumination beam bundle running coaxially to an observation beam path or observation beam bundle. The illumination device is hereby characterized according to the invention in that the light source lies in the front focal point of the collector and that the at least one illumination optics unit is designed in such a way that the light source is/will be imaged on the fundus of the eye to be observed.

In particular, a one-stage stereo-coaxial illumination can be provided by the illumination device according to the invention. The illumination device according to the invention produces a homogeneous “red reflex”. The basic feature of the present invention consists of the fact that the light source lies in the front focal point of the collector. Advantageously, the light source is imaged coaxially to the observation on the object to be observed, for example, the fundus of a patient’s eye that is to be observed.

In comparison with the solution known from the prior art, the one-stage illumination according to the invention dispenses with a Köhler illumination and thus omits an imaging of a luminous-field diaphragm and an aperture diaphragm. In this way, the structural space necessary for the illumination device can be reduced. Also, the illumination device can be built in a structurally simple manner, which is of advantage in many cases.

A true coaxial illumination will be created with the present invention. “Coaxial” is therefore generally understood as an illumination near the axis. This includes both an illumination at precisely zero degrees as well as an oblique illumination at a very small angle close to the axis. Therefore, solutions with slight deviations from a system of coaxial illumination are also included by the present invention.

According to the invention, the illumination device is provided for an observation device, but the invention is not limited to specific types of observation devices. For example, but not exclusively, the observation device can involve an operating microscope. Several non-exclusive examples for possible applications in the field of operating microscopes are described in detail in connection with the observation device according to the invention.

In the simplest case, a single illumination beam path with one illumination beam bundle is provided. However, embodiments with one illumination beam path having two or more illumination beam bundles are also possible or even embodiments with two or more illumination beam paths, each illumination beam path in turn having at least one illumination beam bundle.

According to the invention, it is additionally provided that the illumination device has an illumination optics unit configured in a special manner. First of all, this illumination optics unit is characterized in that it has a collector. This collector can advantageously comprise one or more individual or combined lens element(s). According to the invention, the illumination optics unit is constructed in such a way that the light source lies in the front focal point of the collector.

According to the invention, the at least one illumination optics unit is designed in such a way that the light source is imaged on the object to be observed, particularly on the fundus of an eye to be observed. If the object to be observed involves an eye, the cornea of the eye can be illuminated telecentrically or approximately telecentrically with the illumination device according to the invention. In addition, the eye images the light source again on the retina, in a variable manner according to the refractive error of the eye. This light is then reflected at the red retina and illuminates uniformly, intensively and in a contrast-rich manner the lens of the eye that is to be operated on.

Advantageously, the illumination device can have at least one objective element. The objective element can also be designed as an objective element of an observation device, in particular as its principal objective. However, this is not absolutely necessary.

It may preferably be provided that the objective element is a component of the collector. If the objective element is also the principal objective of an observation device, then the principal objective also will be a component of the collector. In such a case, the coaxial superimposition of observation and illumination advantageously occurs above the objective element, for example, above a principal objective of an observation device.

The coaxial superimposition of observation and illumination, however, may also occur below the objective element, for example, below a principal objective of an observation device. However, the objective element is then no longer a component of the collector.

In order to avoid stray light, the objective element can be disposed tilted—within tolerable limits—preferably also in combination with a means for avoiding stray light, which is described further below.

In another configuration, a covering element, particularly a covering glass, can be provided in the beam course, below the objective element. In order to avoid stray light, the covering element can be disposed tilted—within tolerable limits—also in combination with a means for avoiding stray light, which is described further below.

Advantageously, means can be provided in order to coaxially superimpose at least one observation beam bundle and at least one illumination beam bundle in each case. These means can be configured in the most diverse ways and disposed in the most diverse places. Several non-exclusive examples will be explained below for this purpose.

For example, it may be provided that the means for superimposing are disposed in such a way that a superimposition of the observation beam bundle and the illumination beam bundle is made above the objective element. The superimposition of the observation beam bundle and the illumination beam bundle can be made, for example, in the parallel beam path above the principal objective.

For example, it may be provided that the means for superimposing are disposed in such a way that a superimposition of the observation beam bundle and the illumination beam bundle is made below the objective element. The possibility thus also exists of superimposing the illumination beam bundle and the observation beam bundle below the principal objective. It is advantageous in this case, if the illumination beam bundles are inclined, corresponding to the focal depth of the principal objective.

As has been stated above, the invention is not limited to specific configurations of “superimposition means”. For example, the means for superimposing can have at least one optical element in the form of a prism and/or a beam-splitting plate and/or a mirror, e.g., a partially transparent mirror and/or a perforated mirror. Of course, the means may also be configured in another way, so that the invention is not limited to the named examples.

In another configuration, the illumination device can advantageously have at least one optical element for avoiding stray light. This element may involve, for example, a diaphragm, which can be configured as a fixed or variable diaphragm.

As was stated above, the invention is not limited to a specific number of light sources or their configuration. For example, two or more light sources may be provided, each light source producing an illumination beam path or an illumination beam bundle. Thus, independent light sources can be used, whereby each light source produces its own partial illumination beam bundle. Or, however, only a single light source can be provided, whereby means are provided for dividing the illumination beam path or the illumination beam bundle of the light source into two or more illumination beam paths or illumination beam bundles. Here, suitable beam splitters may be used in the form of prisms, partially transparent mirrors and similar means.

Preferably, the illumination device can be designed for generating two illumination beam paths or two illumination beam bundles, whereby the axes of the illumination beam paths or illumination beam bundles, in particular, are inclined relative to the plane of symmetry. In this case, the inclination of the illumination axes to the plane of symmetry can be selected or will be selected advantageously corresponding to the stereo angle of the observation. In particular, such an inclination will imply that the principal objective element of an observation device is not a component of the illumination device and thus is not an element of the illumination device. The illumination device in this case particularly does not have an objective element.

In another configuration, the illumination device can have at least one additional illumination device for illumination far from the axis. In this case, it may involve, for example, a self-contained illumination device, for example, for a surrounding-field illumination. However, it is also conceivable to provide a common coaxial and surrounding-field illumination, for example, by means of a second illumination optics unit or illumination via beam splitting.

The present invention is not limited to the use of specific light sources. Several nonexclusive, advantageous examples will be named below for this purpose. For example, the at least one light source can be designed as a lamp, in particular as a halogen lamp or a xenon lamp, as a laser, as a non-thermal radiator, as a light guide, in particular as an optical-fiber light guide bundle, as at least one LED (light-emitting diode), as at least one OLED (organic light-emitting diode), or similar source. Of course, combinations of different light sources are also possible.

Advantageously, the light source is formed from a system of one or more miniature light source(s) that can be switched on individually or by regions. The illumination device is configured in such a way that it can be varied in a simple manner with respect to the geometry of the luminous field that it produces. In this way, the miniature light sources will be controlled—in particular, electronically—from the outside, preferably by a control device. Another feature provides that the miniature light sources can be controlled at least in regions, in order to be able to adjust variable lighting geometries. This is particularly of advantage in the case of the generation of annular illumination beam bundles. The invention is thereby not limited to specific sizes and/or shapes of regions. In the simplest case, a single point can be controlled in such a way. Particularly when the luminous source is formed from a matrix composed of individual miniature light sources, one or more miniature light sources can be controlled individually or in groups, whereby in the last-named case, individual miniature light sources can be combined into one region. Also, in this respect, the invention is not limited to concrete embodiments.

Advantageously, the light source can be formed from a system of one or more light diode(s) (LEDs), in particular organic light diode(s) (OLEDs). Organic light diodes were originally developed as microdisplays. Unlike LCDs, which require a backlighting, OLEDs by themselves illuminate as Lambert radiators (surface or flat emitters).

As patterned illumination sources, OLEDs offer a good light efficiency and small structures without intermediate dark spaces. Depending on the desired lighting geometry, individual miniature light sources can be turned on and others can remain turned off. The filling factor is higher in OLEDs as opposed to LEDs, which means that a higher packing density can be provided. The use of a display of LEDs or OLEDs makes possible a programmable switching, and also, for example, the switching of different lighting modes that can be automated, without having to move mechanical components, such as, e.g., phase contrast rings, filters, reducers and similar components. Particularly suitable, for example, are white OLEDs, whose spectrum is determined by a mixture of organic molecules.

In another configuration, for the coaxial illumination of two observation beam paths, a common illumination optics unit or two separate illumination optics units can be provided. In particular, for the coaxial illumination of two observation beam paths or observation beam bundles, the observation beam paths or observation beam bundles of the collector can be produced, for example, by a common illumination optics unit or two separate illumination optics units. For example, in the case of several illumination beam paths or illumination beam bundles, it can be provided that each illumination beam path or each illumination beam bundle has its own illumination optics unit. In another configuration, a single, common illumination optics unit can be provided for each illumination beam path or each illumination beam bundle.

The illumination device can be designed particularly advantageously as an illumination device in an operating microscope, in particular in an ophthalmologic observation device, preferably in an operating microscope designed for cataract extraction.

According to a second aspect of the invention, an observation device is provided, particularly an operating microscope, having one, two or more observation beam paths, each having at least one observation beam bundle, and with an illumination device having at least one light source for producing at least one illumination beam path having at least one illumination beam bundle for illuminating an object to be observed, in particular, an eye to be observed, the illumination device having at least one illumination optics unit, which has a collector, and the at least one illumination beam path or the at least one illumination beam bundle running coaxially to the observation beam path or observation beam bundle. It is provided according to the invention that the light source lies in the front focal point of the collector and that the at least one illumination optics unit is designed in such a way that the light source is imaged on the fundus of the eye to be observed.

Advantageously, the illumination device is designed in the way described above, according to the invention, so that reference is made to the corresponding description.

The observation device may have, for example, a principal objective element, which is identical to the objective element of the illumination device, whereby means are provided in order to superimpose in each case an observation beam path or an observation beam bundle and an illumination beam path or an illumination beam bundle, and whereby means for superimposing are disposed in such a way that a superimposition of observation beam path or observation beam bundle and illumination beam path or illumination beam bundle is made above the principal objective element.

In another configuration, the observation device can have a principal objective element, which is not identical to an element of the illumination device, whereby means are provided in order to superimpose in each case an observation beam path or an observation beam bundle and an illumination beam path or an illumination beam bundle, and whereby means for superimposing are disposed in such a way that a superimposition of observation beam path or observation beam bundle and illumination beam path or illumination beam bundle is made below the principal objective element.

The observation device can advantageously be designed as an operating microscope, in particular as an ophthalmologic observation device, preferably as an operating microscope designed for cataract extraction.

BRIEF DESCRIPTION OF THE DRAWINGS

The invention will now be explained in more detail on the basis of embodiment examples with reference to the appended drawings. Here

DETAILED DESCRIPTION OF THE INVENTION

Figure 1:
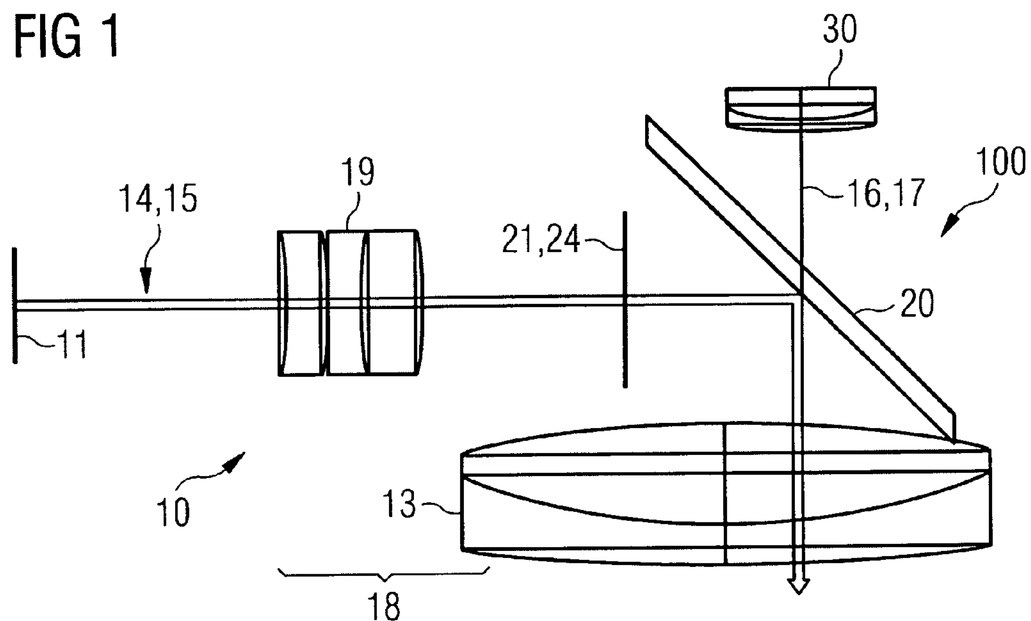
FIG. 1 shows a lateral view of a first example of embodiment of an illumination device according to the invention.

Shown in each of FIGS. 1 to 7 is an illumination device 10, which is used as an illumination device in an operating microscope 100, particularly in an ophthalmologic observation device, preferably in an operating microscope designed for cataract extraction. Operating microscope 100 has two observation beam paths 16, 17, in which additional optical elements 30 can be provided, but which will not be discussed in more detail in the following.

Embodiment examples are shown in the figures, in which the illumination device has an objective element 13, which is also shown simultaneously as the principal objective of operating microscope 100.

Figure 2:
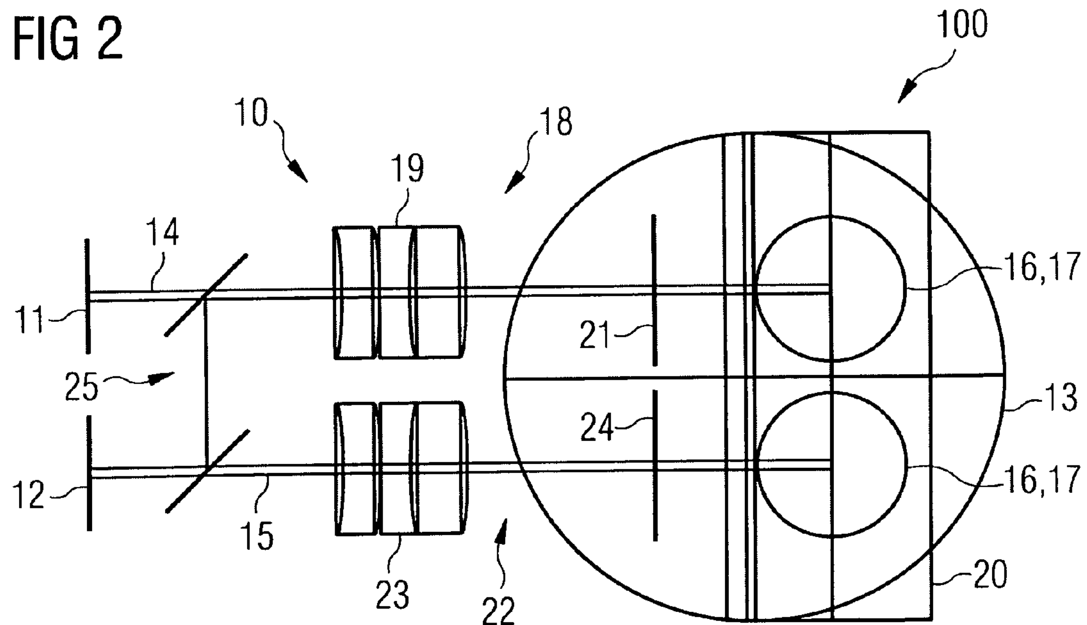
FIG. 2 shows a top view of the illumination device shown in FIG. 1.

As is shown in FIGS. 1 and 2, illumination device 10 first provides at least one light source 11 for generating at least one illumination beam path 14, 15 with at least one illumination beam bundle, which will be superimposed coaxially with at least one observation beam path 16, 17 or observation beam bundle. A coaxial illumination will be produced by light source 11. The light produced by light source 11 passes through an illumination optics unit in the form of a collector 18 having a number of collector lenses 19, whereby it is provided according to the invention that the light source 11 lies in the front focal point of collector 18. Objective element 13, which also represents the principal objective of operating microscope 100, is a part of collector 18 in the example shown. Thus, the illuminating light can be imaged coaxially to the observation onto the fundus of an eye to be observed, if a deflecting element 20 is provided. This deflecting element 20 represents an optical element for the coaxial superimposing of observation beam paths 16, 17 and illumination beam paths 14, 15, and can be designed, for example, as a partially transparent mirror or the like. In order to avoid stray light, in addition, an appropriate means 21, 24, for example, a diaphragm, can be provided.

Two light sources 11, 12 can be provided, each of which produces an illumination beam path 14, 15 and each of these paths has at least one illumination beam bundle. Each illumination beam path 14, 15 passes through its own illumination optics unit in the form of a collector 18, 22. Each collector 18, 22 has a number of collector lenses 19, 23. Only one objective element 13, however, is provided and this represents a component of both collectors 18, 22. A diaphragm 21, 24 for avoiding stray light is found in each illumination beam path 14, 15. Light sources 11,12 in turn lie in the front focal point of collectors 18, 22. Illumination beam paths 14, 15 are deflected by a common deflecting element 20 and superimpose observation beam paths 16, 17. Alternatively, only a single light source can be provided, which is then split into two illumination beam paths 14, 15 via suitable beam-splitting means 25.

Figure 3:
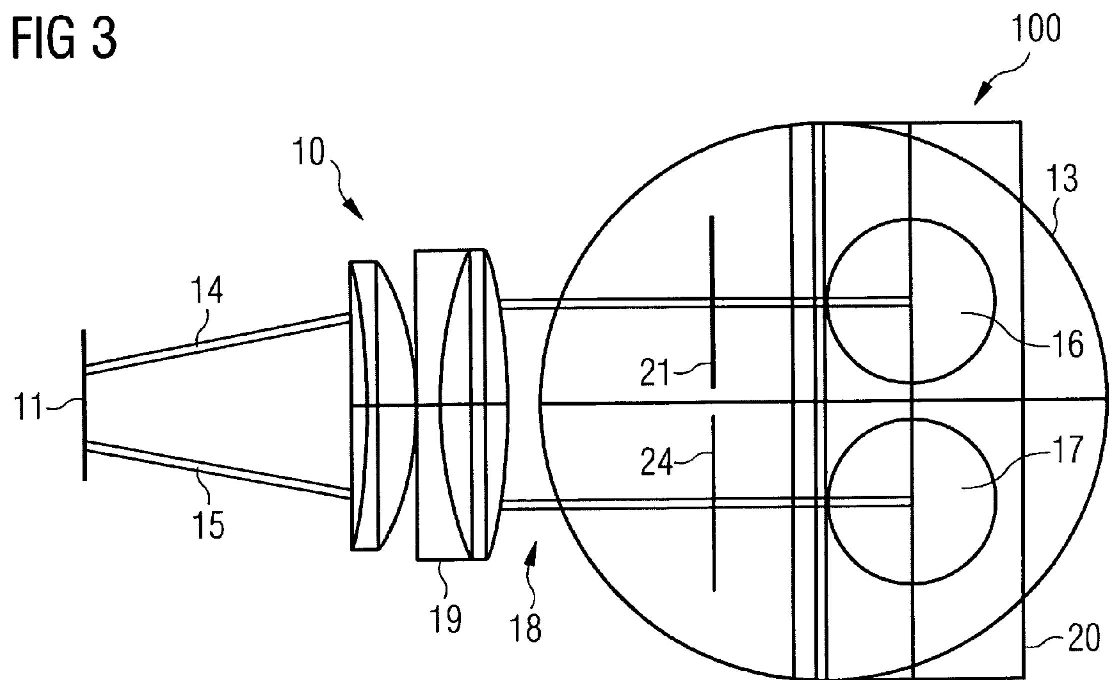
FIG. 3 shows a top view of a first alternative and a second alternative of the illumination device shown in FIG. 1.

A first alternative of illumination device 10 shown in FIG. 1 is shown in FIG. 3. In this example of embodiment, two light sources 11, 12 are provided, each of which produces an illumination beam path 14, 15 and each of these paths has at least one illumination beam bundle. Each illumination beam path 14, 15 passes through a single common illumination optics unit in the form of a collector 18. Collector 18 has a number of collector lenses 19. Only one objective element 13, however, is provided and this represents a component of both collectors 18. A diaphragm 21, 24 for avoiding stray light is found in each illumination beam path 14, 15. Light sources 11, 12 in turn lie in the front focal point of collector 18. Illumination beam paths 14, 15 are deflected by a common deflecting element 20 and superimpose observation beam paths 16, 17. Alternatively, only a single light source can be provided, which is then split into two illumination beam paths 14, 15 via suitable beam-splitting means.

Figure 4:
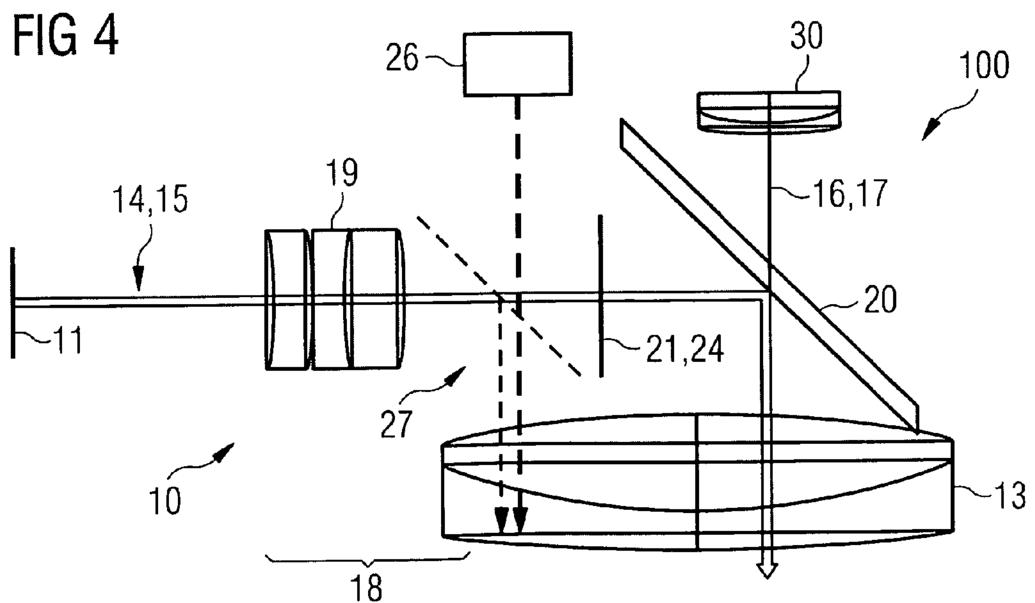
FIG. 4 shows a lateral view of a third alternative of the illumination device shown in FIG. 1.

The example of embodiment shown in FIG. 4 corresponds in its basic structure to the example shown in FIG. 1, so that first of all, reference is made to the full extent to this example in order to avoid repetition. Here, the same components are provided with the same reference numerals. Additionally, illumination device 10 shown in FIG. 4 also provides an additional illumination device for illumination far from the axis. This may involve, for example, a separate illumination device 26 for producing a surrounding-field illumination. Alternatively, it is also conceivable that only a single illumination device is used, whereby the simultaneous generation of a coaxial illumination and a surrounding-field illumination is produced by suitable beam-splitting means 27.

Figure 5:
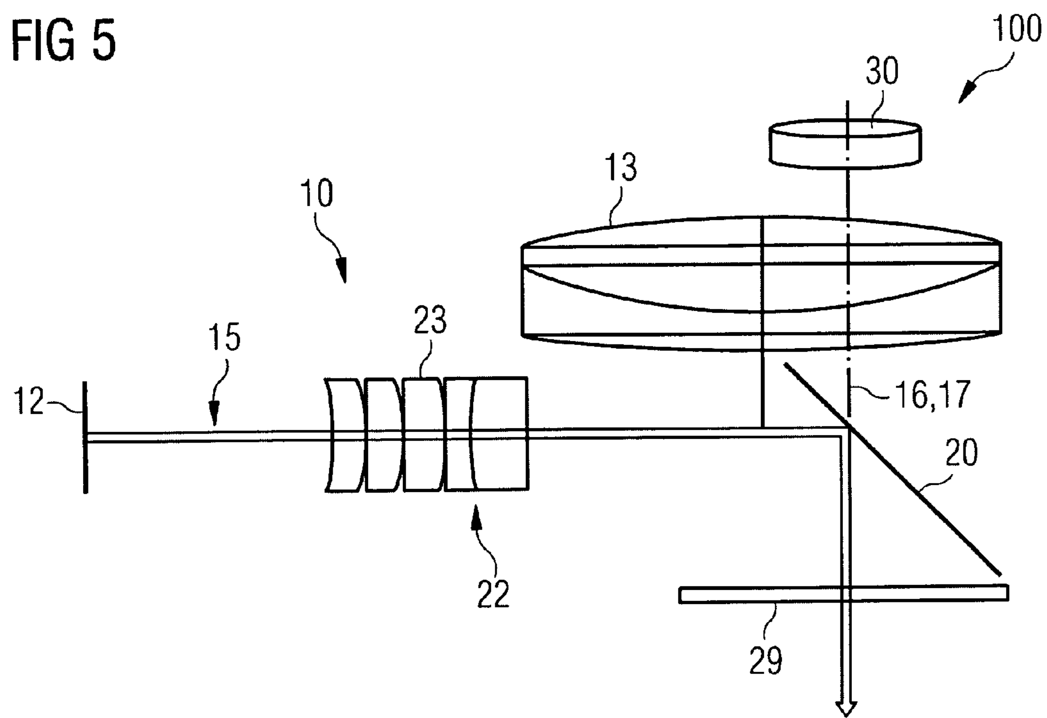
FIG. 5 shows a lateral view of a second example of embodiment of an illumination device according to the invention.
Figure 6:
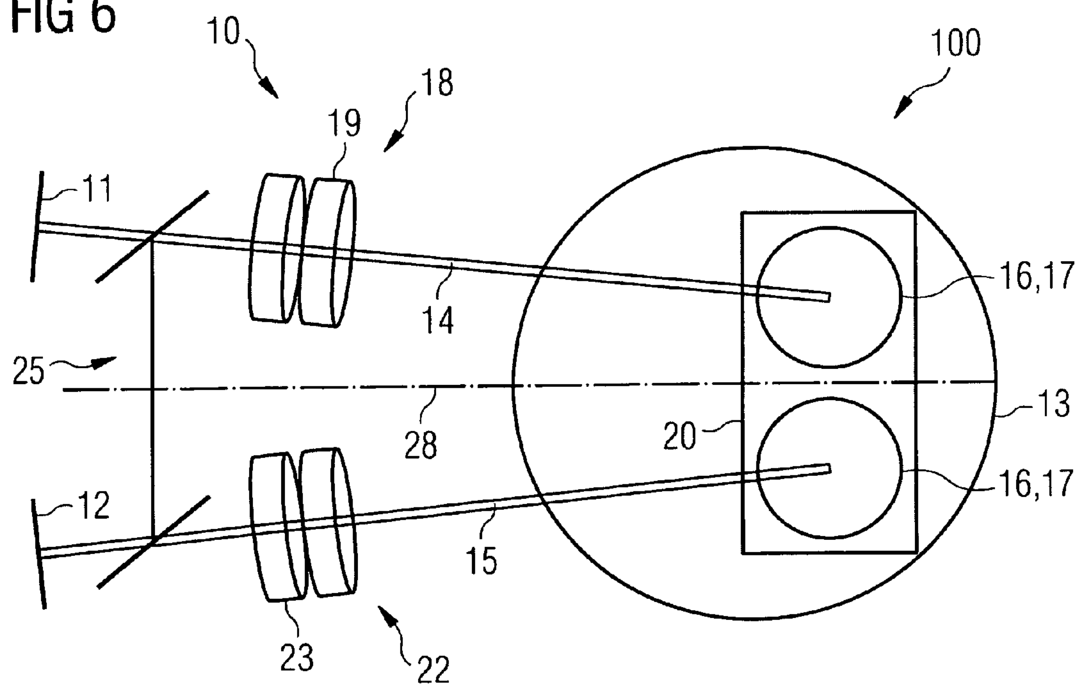
FIG. 6 shows a top view and a first alternative of the illumination device shown in FIG. 5.
Figure 7:
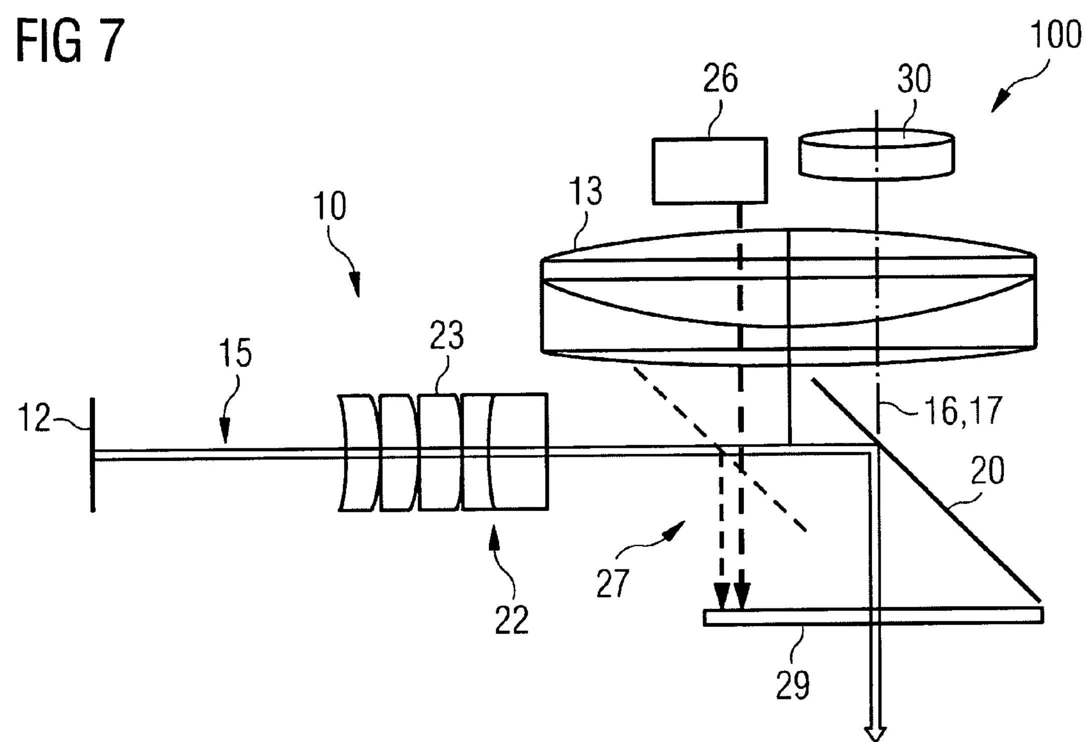
FIG. 7 shows a lateral view of a second alternative of the illumination device shown in FIG. 5.

Another embodiment is shown in FIGS. 5 to 7, in which the illumination beam paths 14, 15 are not superimposed with observation beam paths 16, 17 above objective element 13, but rather they are superimposed below objective element 13.

A variant is shown in FIGS. 5 and 6, in which two light sources 11, 12 produce two illumination beam paths 14, 15. Each illumination beam path 14, 15 passes through a collector

18, 22, with corresponding collector lenses 19, 23. In this case, objective element 13 does not represent a component of collectors 18, 22. Here also, light sources 11, 12 in turn lie in the front focal point of collectors 18, 22. Illumination beam paths 14, 15 are superimposed with observation beam paths 16, 17 in turn via a common deflecting element 20 in the form of a partially transparent mirror.

In the examples shown in FIGS. 5 to 7, each illumination beam path 14, 15 is provided with its own illumination optics unit, which in turn has its own collector 18, 22. Two light sources 11, 12 can also be provided. Alternatively, only one light source is also conceivable, which is divided by means of a beam-splitting means 25. It can be advantageously provided that the illumination axes are inclined relative to the plane of symmetry 28, preferably corresponding to the stereo angle of the observation.

A covering glass 29 can additionally be provided in the examples shown in FIGS. 5 to 7. Covering glass 29 can be tilted in order to avoid stray light. Also, as described in connection with FIG. 4, additional illumination devices 26, 27 can be provided for illumination far from the axis. This is shown in FIG. 7.

The illumination devices 10 shown in FIGS. 1 to 7 produce a homogeneous "red reflex". Light sources 11, 12 lie in the front focal point of collectors 18, 22 and are imaged on the object to be observed, for example, the fundus of an eye, coaxially to the observation beam paths 16, 17. Objective element 13 can be a component of collectors 18, 22, as is shown in connection with FIGS. 1 to 4. Optical elements in the form of deflecting elements 20 are provided, which can be designed as partially transparent mirrors, for superimposing illumination beam paths 14, 15 and observation beam paths 16, 17. Suitable means 21, 24, e.g., in the form of a diaphragm, can be provided, in order to avoid stray light.

Illumination beam paths 14, 15 and observation beam paths 16, 17 can also be coaxially superimposed below objective element 13, as is shown in FIGS. 5 to 7. Objective element 13 is then no longer a component of collectors 18, 22.

Additional illumination means 26, 27 can be provided in order to illuminate far from the axis, for example, with a second illumination device 26, or by creating a common coaxial and surrounding-field illumination by using beam-splitting means 27.

For the coaxial illumination of two observation beam paths 16, 17, the illumination beam paths 14, 15 of the collector can be produced by a common illumination optics unit or by separate illumination optics units.

Also, in order to avoid stray light, objective element 13 or, if present, a covering glass 29, can be tilted in combination with diaphragms 21, 24, within tolerable limits.

Halogen lamps or xenon lamps, one or two light guides, LEDs or similar means can be used as light sources 11, 12.

LIST OF REFERENCE NUMERALS

10 Illumination device
11 Light source
12 Light source
13 Objective element
14 Illumination beam path
15 Illumination beam path
16 Observation beam path
17 Observation beam path
18 Collector
19 Collector lenses
20 Deflecting element
21 Means for avoiding stray light (diaphragm)
22 Collector
23 Collector lenses
24 Means for avoiding stray light (diaphragm)
25 Beam-splitting means
26 Additional illumination device
27 Beam-splitting means
28 Plane of symmetry
29 Covering element (covering glass)
30 Optical element
100 Observation device (operating microscope)

What is claimed is:

1. An illumination device for an observation device having one, two or more observation beam paths, each with at least observation beam bundle, particularly for an operating microscope, the illumination device having at least one light source for producing at least one illumination beam path with at least one illumination beam bundle for illuminating an object to be observed, in particular, an eye to be observed, the illumination device having at least one illumination optics unit, which has a collector, and the at least one illumination beam path or the at least one illumination beam bundle running coaxially to an observation beam path or observation beam bundle, hereby characterized in that the illumination device is adapted to provide a one-stage illumination that omits an imaging of a luminous-field diaphragm and an aperture diaphragm, in that the light source lies in the front focal point of the collector and that the at least one illumination optics unit is designed in such a way that light source is/will be imaged on the fundus of the eye to be observed.

2. The illumination device according to claim 1, further characterized in that it has an objective element.

3. The illumination device according to claim 2, further characterized in that objective element is also designed as an objective element of an observation device, in particular as its principal objective.

4. The illumination device according to claim 2 or 3, further characterized in that objective element is a component of collector.

5. The illumination device according to claim 1, further characterized in that means are provided in order to coaxially superimpose at least one observation beam bundle and at least one illumination beam bundle in each case.

6. The illumination device according to claim 5, further characterized in that means for superimposing has at least one optical element in the form of a prism and/or a beam-splitting plate and/or a partially transparent mirror and/or a perforated mirror.

7. The illumination device according to claim 1, further characterized in that this device has at least one optical element for avoiding stray light.

8. The illumination device according to claim 2, further characterized in that objective element is arranged tilted in order to avoid stray light.

9. The illumination device according to claim 1, further characterized in that a covering element, particularly a covering glass, is provided in the beam path below objective element.

10. The illumination device according to claim 9, further characterized in that covering element is tilted in order to avoid stray light.

11. The illumination device according to claim 1, further characterized in that two or more light sources are provided and that an illumination beam path or an illumination beam bundle will be produced by means of each light source, or that a single light source is provided and that means are provided for splitting the illumination beam path or the illumination beam bundle of the light source into two or more illumination beam paths or illumination beam bundles.

12. The illumination device according to claim 1, further characterized in that this device is designed for generating two illumination beam paths or two illumination beam bundles and that the axes of the illumination beam paths or illumination beam bundles, in particular, are inclined relative to the plane of symmetry.

13. The illumination device according to claim 1, further characterized in that this device has at least one additional illumination device for illumination far from the axis.

14. The illumination device according to claim 1, further characterized in that the at least one light source is designed as a lamp, in particular as a halogen lamp or a xenon lamp, as a laser, as a non-thermal radiator, as a light guide, particularly as an optical-fiber light guide bundle, as at least one LED, or at least one OLED.

15. The illumination device according to claim 1, further characterized in that for the coaxial illumination of two observation beam paths, a common illumination optics unit or two separate illumination optics units are provided.

16. The illumination device according to claim 1, further characterized in that it is used as an illumination device in an operating microscope, particularly in an ophthalmologic observation device, preferably in an operating microscope designed for cataract extraction.

17. An observation device, particularly an operating microscope, having one, two or more observation beam paths, each having at least one observation beam bundle and having an illumination device with at least one light source for producing at least one illumination beam path with at least one illumination beam bundle for illuminating an object to be observed, in particular, an eye to be observed, the illumination device having at least one illumination optics unit, which has a collector, and the at least one illumination beam path or the at least one illumination beam bundle running coaxially to an observation beam path or observation beam bundle, hereby characterized in that the illumination device is adapted to provide a one-stage illumination that omits an imaging of a luminous-field diaphragm and an aperture diaphragm, in that the light source lies in the front focal point of the collector and that the at least one illumination optics unit is designed in such a way that light source is/will be imaged on the fundus of the eye to be observed.

18. The observation device according to claim 17, further characterized in that observation device has a principal objective element, which is identical to an objective element of illumination device, that means is provided in order to superimpose in each case an observation beam path or an observation beam bundle and an illumination beam path or an illumination beam bundle, and that means for superimposing is disposed in such a way that a superimposition of observation beam path or observation beam bundle and illumination beam path or illumination beam bundle is made above principal objective element.

19. The observation device according to claim 17, further characterized in that observation device has a principal objective element, which is not an element of illumination device, and that means is provided in order to superimpose in each case an observation beam path or an observation beam bundle and an illumination beam path or an illumination beam bundle, and that means for superimposing is disposed in such a way that a superimposition of observation beam path or observation beam bundle and illumination beam path or illumination beam bundle is made below principal objective element.

20. The observation device according to claim 17, further characterized in that this device is designed as an operating microscope, particularly as an ophthalmologic observation device, preferably as an operating microscope designed for cataract extraction.

* * * * *